(12) United States Patent
Nishino et al.

(10) Patent No.: US 8,848,188 B2
(45) Date of Patent: Sep. 30, 2014

(54) FLUORESCENCE MEASUREMENT METHOD AND FLUORESCENCE MEASUREMENT DEVICE

(75) Inventors: Norikazu Nishino, Kitakyushu (JP); Mitsuhiro Fukamachi, Tokyo (JP); Fumio Obayashi, Tokyo (JP)

(73) Assignees: Peptide Support Ltd., Fukuoka (JP); The Yoshida Dental Mfg. Co., Ltd., Tokyo (JP)

(*) Notice: Subject to any disclaimer, the term of this patent is extended or adjusted under 35 U.S.C. 154(b) by 0 days.

(21) Appl. No.: 13/825,572

(22) PCT Filed: Sep. 28, 2011

(86) PCT No.: PCT/JP2011/005469
§ 371 (c)(1),
(2), (4) Date: Jun. 10, 2013

(87) PCT Pub. No.: WO2012/042870
PCT Pub. Date: Apr. 5, 2012

(65) Prior Publication Data
US 2013/0260405 A1    Oct. 3, 2013

(30) Foreign Application Priority Data
Sep. 28, 2010   (JP) .................. 2010-217958

(51) Int. Cl.
*G01N 21/00* (2006.01)
*G01N 21/64* (2006.01)
*G01N 21/03* (2006.01)

(52) U.S. Cl.
CPC .... *G01N 21/6486* (2013.01); *G01N 2021/0367* (2013.01); *G01N 21/0303* (2013.01); *G01N 21/645* (2013.01)
USPC ......................... 356/432; 356/436

(58) Field of Classification Search
CPC .................. G01N 27/44721; G01N 27/44782; G01N 15/1434; G01N 15/147; G01N 15/1484; G01N 2015/149; G01N 2015/1497; G01N 2021/0367; G01N 2021/6484; G01N 2035/1034; G01N 21/00; G01N 21/03; G01N 21/0303
See application file for complete search history.

(56) References Cited

U.S. PATENT DOCUMENTS

| 4,291,230 A * | 9/1981 | Heiss .......................... 250/458.1 |
| 2010/0136709 A1* | 6/2010 | Ruckstuhl et al. ............ 436/164 |
| 2010/0208256 A1* | 8/2010 | Tang et al. .................... 356/326 |

FOREIGN PATENT DOCUMENTS

| JP | 06-034546 | 2/1994 |
| JP | 08-500183 | 9/1996 |
| JP | 2004-163257 | 6/2004 |
| JP | 2004-325431 | 11/2004 |
| JP | 2004-357347 | 12/2004 |
| JP | 2005-140683 | 6/2005 |
| JP | 2005-201859 | 7/2005 |
| JP | 2007-521485 A | 2/2007 |
| JP | 2007-113996 | 5/2007 |
| JP | 2007-519923 A | 7/2007 |
| JP | 2008-185440 | 8/2008 |
| JP | 2008-541139 A | 11/2008 |
| JP | 2008-289437 | 12/2008 |
| JP | 2010-122146 | 6/2010 |
| JP | 2010-190713 | 9/2010 |

OTHER PUBLICATIONS

PCT/JP2011/005469, Translation of the International Report on Patentability dates Apr. 25, 2013.

* cited by examiner

*Primary Examiner* — Michael P Stafira
(74) *Attorney, Agent, or Firm* — Chaniey P. Singleton; Edwin S. Flores; Chalker Flores, LLP

(57) ABSTRACT

In order to provide a fluorescence measurement method and a fluorescence measurement device that are provided by a simpler structure, and are more inexpensive and capable of measuring an amount of fluorescence using a very small amount of sample, using a fluorescence measurement device including a light-blocking measurement box to which a microtube is loaded; a container support part disposed inside the measurement box, the container support part vertically supporting the microtube; an excitation light source part disposed inside the measurement box, the excitation light source part including a light source that horizontally irradiates excitation light a sidewall surface of the loaded microtube; and a fluorescence detection part provided at an upper portion of the measurement box and above the loaded microtube, the fluorescence detection part measuring an amount of fluorescence in a particular wavelength range from a target sample, a microtube charged with a target liquid sample is loaded into the measurement box, the microtube that is uncapped is irradiated laterally in a horizontal direction with excitation light having a particular peak wavelength, and an amount of fluorescence from the target liquid sample excited by light distributed to the entire region of the target liquid inside the tube using a sidewall surface of the microtube as an excitation light waveguide and light leaking from the sidewall surface is measured by a fluorescence detection part for a particular wavelength range.

15 Claims, 8 Drawing Sheets

FLUORESCENCE MEASUREMENT METHOD AND FLUORESCENCE MEASUREMENT DEVICE

CROSS-REFERENCE TO RELATED APPLICATIONS

This application is the National Stage of International Application No. PCT/JP2011/005469, filed on 28 Sep. 2011 claiming the priority of JP 2010-217958 filed on 28 Sep. 2010, the content of each of which is incorporated by reference herein.

TECHNICAL FIELD

The present invention relates to a fluorescence measurement method and a fluorescence measurement device in which a microtube charged with a target liquid sample is loaded, and the microtube that is uncapped is irradiated laterally in a horizontal direction with excitation light having a particular peak wavelength to measure fluorescence by a fluorescence detection part for a particular wavelength range provided above the microtube.

BACKGROUND ART

In recent years, fluorescence detection devices have been used in a wide range of areas such as medical diagnoses based on quantitative change of, e.g., an enzyme where a disease is induced by, e.g., a proteolytic enzyme, environmental evaluations using an enzyme activity as a marker for, e.g., microorganisms existing in the environment, and monitoring operations in detection systems in which a fluorescence intensity is successively increased by a chemical reaction.

As an example of such fluorescence detection device, a fluorescence detection device has been proposed, which includes: a sample container that holds a sample; a container holding part that holds the sample container, the container holding part being capable of changing a temperature of the sample in the sample container; a fluorescence detector for measuring fluorescence from the sample; and a light source that emits excitation light for exciting a sample for fluorescence emission, wherein the light source and the container holding part, and the container holding part and the fluorescence detector are optically connected via respective optical fibers, and the optical fibers are installed in the container holding part so as to excite the sample in the container for fluorescence emission from the underneath of the sample container held by the container holding part and receive fluorescence emitted by the sample from the underneath of the sample container (see, for example, patent document 1). However, where excitation irradiation is performed from a bottom portion of a microtube such as an Eppendorf tube, the control in thickness and shape of the bottom portion cannot be considered sufficient because of the tube manufacturing process, resulting in wide optical variations.

For other examples, there have been proposed a fluorescence measurement device in which a liquid-state sample arranged at an excitation light converging position for an objective lens of an epi-illumination optical system using a fluorescent cube is held in a hole of a sample holding plate, the hole extending through the sample holding plate in parallel to an optical axis (see, for example, patent document 2); a fluorescence measurement device including a light source that emits excitation light, a sensor part that propagates the excitation light entered from an end thereof inside and emits evanescent light from another end thereof, and excites a fluorescent substance by the excitation light, the fluorescent substance indicating existence of a measurement target substance in a sample liquid in which the other end is immersed, and an photodetector that detects fluorescence emitted from the fluorescent substance by the excitation, wherein the sensor part includes a substantially-columnar sensor part body and a cylindrical cover portion surrounding the sensor part body via a space between an outer peripheral surface of the sensor part body at least adjacent to the other end and the cylindrical cover portion, and wherein the cover portion includes an occlusion portion that occludes the space at an end portion of the cover portion on the other end side (see, for example, patent document 3); an enzyme activity measurement device at least including a laser light source for near-infrared femtosecond laser light for inducing a process of multiphoton excitation of a substrate or a product of substrate metabolism, a radiation wave detection part that detects radiation wave generated from the process of multiphoton excitation of the substrate or the product of substrate metabolism; and an optical path that guides the near-infrared femtosecond laser light to a site where an enzyme exists and guides the radiation wave to the radiation wave detection part (see, for example, patent document 4); a fluorescence measurement device including a light source for exciting a fluorescence substance in a sample, a collecting lens that collects fluorescence emitted from the fluorescence substance, a spatial filter that transmits the fluorescence collected by the collecting lens, an photodetector that detects the fluorescence that has passed through the spatial filter, a signal analysis part that analyzes an output signal from the photodetector, and an adjustment part that adjusts an arrangement position of at least one of the collecting lens and the spatial filter based on an analysis result obtained by the signal analysis part (see, for example, patent document 5); and a fluorescence detection device including a white light source, an excitation-side light dispersion means for dispersing light emitted from the white light source, an excitation optical system including an image formation optical system not including an optical lens but consisting of a combination of mirrors, the excitation optical system irradiating with the light dispersed by the excitation-side light dispersion means a sample as excitation light, a fluorescence optical system including an image formation optical system not including an optical lens but consisting of a combination of mirrors, the fluorescence optical system collecting fluorescence emitted from the sample excited by the excitation light, a fluorescence-side dispersion means for dispersing the fluorescence collected by the fluorescence optical system, and a detector that detects the fluorescence dispersed by the fluorescence-side dispersion means (see, for example, patent document 6).

Meanwhile, as examples of periodontal disease-causing bacteria, *Porphyromonas gingivalis*, *Treponema denticola* and *Tannerella forsythia* are known, and these bacteria form a bacteria nest inside plaque (biofilm), causing inflammation at an interface between a tooth root and a gum, thereby ingesting blood components for reproduction. It is known that along with the inflammation, neutrophils infiltrate and as a result, the activity of, e.g., released leukocyte elastase increases. Based on such knowledge, test kits for analyzing a sample from a mouth cavity of a patient to detect the patient's periodontal disease have been proposed (see, for example, patent document 7). The test kit includes a first detection assay for detecting a first substance, which is Arg-gingipain derived from the bacterium *P. gingivalis* and a second detection assay for detecting a second substance, which is human neutrophil elastase derived from an immune system or an inflammation system of a patient.

Also, a sheet-like medical product for in vitro diagnosis has been commercially available, which detects β-naphthylamine liberated as a result of a BANA (N-benzoyl-DL-arginylβ-naphthylamido) substrate in a film with a sample applied thereto being degraded using a BANA degradative activity each of three types of bactertia, *P. gingivalis, T. denticola* and *T. forsythia* in subgingival plaque has, to check whether or not these bacteria exist.

PRIOR ART DOCUMENTS

Patent Documents

Patent Document 1: Japanese unexamined Patent Application Publication No. 6-34546
Patent Document 2: Japanese unexamined Patent Application Publication No. 2010-190713
Patent Document 3: Japanese unexamined Patent Application Publication No. 2008-185440
Patent Document 4: Japanese unexamined Patent Application Publication No. 2008-289437
Patent Document 5: Japanese unexamined Patent Application Publication No. 2004-354347
Patent Document 6: Japanese unexamined Patent Application Publication No. 2004-325431
Patent Document 7: Japanese unexamined Patent Application Publication (Translation of PCT Application) No. 2007-519923

SUMMARY OF THE INVENTION

Object to be Attained by the Invention

The conventional fluorescence measurement devices disclosed in the aforementioned patent documents each consist of a complicated configuration and are very expensive, and thus, have been used in the research field, but are not assumed to be used on the clinic level. However, for example, for applications as tools for communications between a patient and a dentist, including periodontal disease diagnosis, inexpensive and simple fluorescence measurement devices are indispensable. Furthermore, in the case of measurement systems using optical fibers, problems inherent to fibers such as end face loss, joint loss and the problem of the material for, e.g., the ultraviolet region cannot be ignored. In particular, in the case of guiding from the bottom portion by a fiber, many problems may occurs in consideration of, e.g., irradiation end face joint structure, dirt on the measurement spot bottom portion and numerical aperture (NA) of the optical fiber as well as material deterioration due to short wavelength.

An object of the present invention is to provide a fluorescence measurement method and a fluorescence measurement device that are provided by a simpler structure, and are more inexpensive and capable of measuring an amount of fluorescence using a very small amount of sample.

Means to Attain the Object

The present inventors have studied for a fluorescence measurement method provided by a more inexpensive structure of a simpler configuration, and focused on the thickness, the shape and the material of a tube, which is not related to the bottom portion structure, reaching an idea of irradiating with excitation light conforming to the characteristics of the thickness, the shape and the material in a transverse direction of the tube in terms of the excitation light irradiation surface; have confirmed that it is possible that a microtube charged with a target liquid sample is loaded into a light-blocking measurement box, the microtube that is uncapped is irradiated laterally in a horizontal direction with excitation light having a particular peak wavelength, and an amount of fluorescence from the target liquid sample excited by light distributed to an entire target liquid inside the tube using a sidewall surface of the microtube as an excitation light waveguide and light leaking from the sidewall surface is measured by a fluorescence detection part for a particular wavelength range provided at an upper portion of the measurement box and above the loaded microtube; and consequently, have found that a role as an optical waveguide, which has generally and conventionally been an idea including an existing optical fiber, can be taken by a side wall of a microtube, and also have confirmed that a fluorescence measurement method according to the present invention eliminates the need for components such as means for dispersing excitation light, a collecting lens, a dichroic mirror and an optical fiber. Furthermore, for optimization that provides a minimum background and a maximum light-reception efficiency, the present inventors have studied on 1) adjustment of a distance between the microtube side wall and a top of the excitation light, 2) a vertical position of a center of excitation light relative to a sample liquid surface of the microtube and 3) adjustment of the level of irradiation energy, and have completed the present invention.

In other words, the present invention relates to: (1) a fluorescence measurement method comprising loading a microtube charged with a target liquid sample is loaded into a light-blocking measurement box, irradiating the microtube that is uncapped laterally in a horizontal direction with excitation light having a particular peak wavelength, and measuring an amount of fluorescence from the target liquid sample excited by light distributed to an entire region of the target liquid inside the tube using a sidewall surface of the microtube as an excitation light waveguide and light leaking from the sidewall surface by a fluorescence detection part for a particular wavelength range provided at an upper portion of the measurement box and above the loaded microtube, (2) the fluorescence measurement method according to (1) above, wherein an ambient temperature of the target liquid sample is controlled; (3) the fluorescence measurement method according to (1) or (2) above, wherein excitation light having a wavelength band of 355 nm to 375 nm is used for irradiation; (4) the fluorescence measurement method according to any one of (1) to (3) above, wherein an LED is used as a light source for the excitation light; (5) the fluorescence measurement method according to any one of (1) to (4) above, wherein the microtube is a plastic microtube that does not block the excitation light; (6) the fluorescence measurement method according to any one of (1) to (5) above, wherein the amount of fluorescence from the target sample is an amount of fluorescence having a wavelength band of 430 nm to 455 nm, and (7) the fluorescence measurement method according to any one of (1) to (6) above, wherein the amount of fluorescence from the target sample is derived from 7-amino-4-methyl-coumarin (hereinafter also referred to as "AMC") or a fluorescent compound similar to 7-amino-4-methyl-coumarin contained in the sample.

The present invention also relates to: (8) a fluorescence measurement device including a light-blocking measurement box to which a microtube is loaded, a container support part disposed inside the measurement box, the container support part vertically supporting the microtube, an excitation light source part disposed inside the measurement box, the excitation light source part including a light source that horizontally irradiates with excitation light a sidewall surface of the loaded microtube, and a fluorescence detection part provided at an upper portion of the measurement box and above the loaded microtube, the fluorescence detection part measuring an amount of fluorescence in a particular wavelength range from a target sample; (9) the fluorescence measurement device according to (8) above, wherein the container support part includes a temperature control means capable of adjusting a temperature of the liquid sample inside the microtube, (10) the fluorescence measurement device according to (8) or (9) above, wherein the excitation light source part includes an LED light source, (11) the fluorescence measurement device according to any one of (8) to (10) above, wherein the excitation light source part includes a light source position control means for horizontally or vertically adjusting a position to be irradiated with excitation light, (12) the fluorescence measurement device according to any one of (8) to (11) above, wherein the fluorescence detection part includes an interference filter, (13) the fluorescence measurement device according to any one of (8) to (12) above, wherein the fluorescence detection part includes a display means for quantifying and displaying an intensity of detected fluorescence, (14) the fluorescence measurement device according to any one of (8) to (13) above, wherein the fluorescence detection part includes a computer for data processing, and (15) a periodontal disease diagnostic device comprising the fluorescence measurement device according to any one of (8) to (14) above.

Effect of the Invention

According to the present invention, a fluorescence detection device capable of, even with an extremely small amount of sample, detecting an amount of fluorescence from the sample, whereby an extremely small amount of sample can easily be obtained non-invasively and extremely safely and analyzed in a short time can be provided extremely inexpensively.

MODE OF CARRYING OUT THE INVENTION

Figure 1:
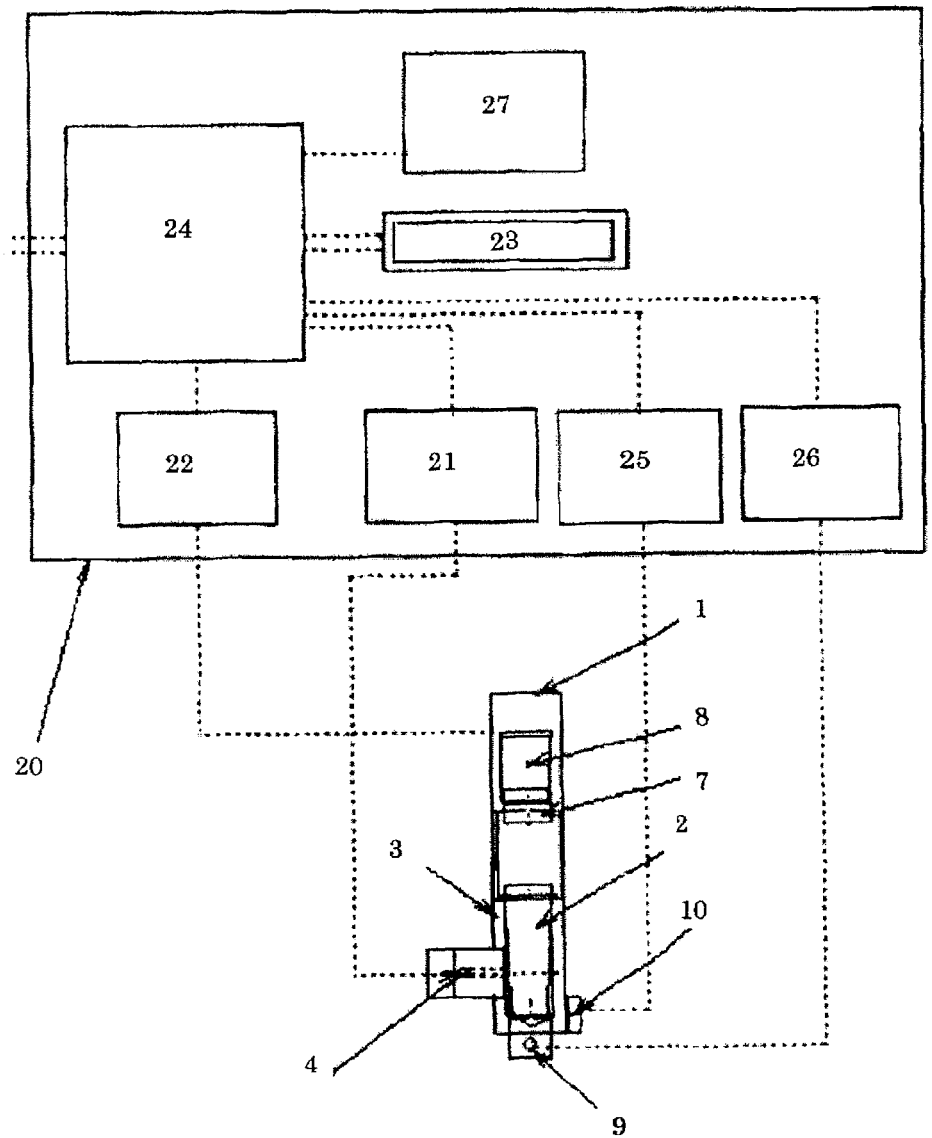
FIG. 1 is a diagram illustrating a basic configuration of a fluorescence measurement device according to the present invention.

A fluorescence measurement method according to the present invention is not specifically limited as long as the method is a method comprising loading a microtube charged with a target liquid sample is loaded into a light-blocking measurement box, irradiating the microtube that is uncapped laterally in a horizontal direction with excitation light having a particular peak wavelength, and measuring an amount of fluorescence from the target liquid sample excited by light distributed to an entire region of the target liquid inside the tube using a sidewall surface of the microtube as an excitation light waveguide and light leaking from the sidewall surface by a fluorescence detection part for a particular wavelength range provided at an upper portion of the measurement box and above the loaded microtube, and also, a fluorescence measurement device according to the present invention is not specifically limited as long as the device is a device including: a light-blocking measurement box to which a microtube is loaded; a container support part disposed inside the measurement box, the container support part vertically supporting the microtube; an excitation light source part disposed inside the measurement box, the excitation light source part including a light source that horizontally irradiates with excitation light a sidewall surface of the loaded microtube; and a fluorescence detection part provided at an upper portion of the measurement box and above the loaded microtube, the fluorescence detection part measuring an amount of fluorescence in a particular wavelength range from a target sample, and the fluorescence measurement device according to the present invention can effectively be used as a periodontal disease diagnostic device. Furthermore, the microtube, which is also referred to as a microcentrifuge tube, is not specifically limited as long as the microtube is a tube having a shape such as a conical shape with its tip closed, which can be capped and can be used for operation, such as reaction, extraction, culture and centrifugal separation, the tube having no effect of attenuation or blocking excitation light having a particular peak wavelength, a sidewall surface of the tube being able to be used as an excitation light waveguide, and for a material for such tube, e.g., plastics or glass, preferably polypropylene or polyethylene, can be used, and a material resistant to organic solvents is preferable. Also, preferable examples of the microtube can include a tube having a volume of 1.0 to 2.0 mL, preferably, 1.5 mL, an outer diameter of 5 to 20 mm, preferably, 8 to 15 mm, and a sidewall thickness of 0.5 to 1.5 mm, preferably, 0.8 to 1.2 mm. Furthermore, in terms of the shape of the microtube, specific examples of the shape can include a microtube of an Assist tube type manufactured by K.K. Assist or a microtube of an Eppendorf tube type manufactured by Eppendorf AG; however, a shape of a microtube having specifications that are substantially the same as those of the above, which is sold by another company, can also be employed.

Examples of a material of the measurement box in the fluorescence measurement device according to the present invention can include metal materials such as aluminum and engineering plastics, which have a light-blocking property and a stiffness that can vertically support the microtube, and also, examples of the container support part disposed inside the measurement box can include a cylindrical hollow structure with an upper portion thereof opened, the structure having a bottom portion that can vertically support the microtube. The microtube charged with a target liquid sample, which is loaded in such container support part, is uncapped and therefore, an amount of fluorescence from the target liquid sample excited by light distributed to the entire region of the target liquid inside the tube using the sidewall surface of the microtube as an excitation light waveguide and light leaking from the sidewall surface can be measured by the fluorescence detection part for a particular wavelength range provided at the upper portion of the measurement box and above the loaded microtube. The light-blocking (property) is not limited to a case where light is perfectly blocked, and is an idea allowing transmission of some light: a total light beam transmittance is preferably not more than 10%, more preferably not more than 5%, further preferably not more than 3%, particularly preferably not more than 1% and above all nearly 0% is preferable.

In the fluorescence measurement method according to the present invention, it is further preferable to control an ambient temperature of the target liquid sample, and thus, it is preferable that the container support part in the fluorescence measurement device according to the present invention includes a temperature control means capable of controlling a temperature of the liquid sample inside the microtube. For such temperature control means, a known one can be used, and for example, a temperature sensor that senses an ambient temperature of the target liquid sample and a temperature control means for comparing a feedback signal from the sensor and a program content designed in advance and outputting an instruction to heat an area in the periphery of the target liquid sample as necessary can be used, and in order to achieve this purpose, e.g., a microcomputer can be used. The ambient temperature of the target liquid sample can be controlled to an optimum temperature for an enzyme or microorganisms in the target liquid sample, for example, 30° C. or 37° C., and a safety control device for the case of abnormal temperature rise may be incorporated for a case where a temperature inside the box increases to 70° C. or more.

In the fluorescence measurement method according to the present invention, for improvement in S/N ratio, it is important to perform control to avoid what is called "overlap", and as one of the means therefor, for excitation light, it is preferable to select a light source for excitation light having a directional characteristic for a smaller angle and a smaller half-value width, and for the directional characteristic, a range of 1° to 45° is preferable, a range of 2° to 30° is more preferable, a range of 3° to 20° is further preferable, and a range of 5° to 15° is particularly preferable. Furthermore, for the half-value width, not more than 40 nm is preferable, not more than 30 nm is more preferable, not more than 20 nm is further preferable, and not more than 10 nm is particularly preferable.

Another means for performing control to avoid the aforementioned "overlap" may include selecting a fluorescent substance to be included in the target liquid sample, the fluorescent substance having a peak wavelength of fluorescence that is off from that of the excitation light to the extent possible, and for example, a fluorescent substance that is not less than 60 nm off from the peak wavelength of the excitation light is preferable, a fluorescent substance that is not less than 70 nm off from the same is more preferable, a fluorescent substance that is not less than 80 nm off from the same is more preferable, a fluorescent substance that is not less than 90 nm off from the same is further preferable, and a fluorescent substance that is not less than 100 nm off from the same is particularly preferable.

The excitation light is not specifically limited as long as the excitation light irradiates laterally in the horizontal direction the microtube that is uncapped, and excites the target liquid sample by means of light distributed to the entire region of the target liquid inside the tube and light leaking from the sidewall surface using the sidewall surface of the microtube as an excitation light waveguide; however, it is preferable that the excitation light irradiates horizontally or substantially horizontally a level equal to or substantially equal to a surface of the target liquid sample inside the tube, and thus, the excitation light source part in the fluorescence measurement device according to the present invention preferably includes a light source position control means for adjusting a position to be irradiated with the excitation light, in the horizontal direction and/or the vertical direction. For such light source position control means, a known vertical and horizontal sliding set can effectively be used.

The excitation light is not specifically limited as long as the excitation light excites a fluorescent substance in the target liquid sample, enabling measurement of an amount of fluorescence from the excited target liquid sample; however, if 7-amino-4-methyl-coumarin or a fluorescent compound similar to 7-amino-4-methyl-coumarin is contained in the target liquid sample, a wavelength band of the excitation light is preferably 330 nm to 400 nm, more preferably 350 nm to 380 nm, further preferably 355 nm to 375 nm, and particularly preferably 360 nm to 370 nm, and such excitation light is preferably used, for example, where a substrate for an enzyme to be examined, which is contained in a sample, is 7-amino-4-methyl-coumarin or a fluorescent compound similar to 7-amino-4-methyl-coumarin.

Specific examples of the light source for the excitation light included in the excitation light source part in the fluorescence measurement device according to the present invention can include xenon lamps, mercury lamps, halogen lamps, laser lights, UV lamps and LEDs (light-emitting diodes); however, LEDs are preferable in terms of: having a small size, being inexpensive and having a long lifetime; having stable temperature characteristics; change in light amount being stabilized in a short time after lighting-up; and being suitable for controlling ultraviolet excited output fluctuation and wavelength fluctuation due to an applied current where a low-price regulated current circuit is used; and an angle of irradiation and a distance of irradiation with excitation light being easily adjusted for optimal injection of the excitation light to the microtube side wall, and above all, an LED having a bombshell-like top shape is particularly preferable, and where such light source is used, there is no need for a complicated configuration using an excitation filter, a collecting lens and a dichroic mirror.

A wavelength band for which an amount of fluorescence from the target sample is measured is preferably a wavelength band of 410 nm to 475 nm, more preferably 425 nm to 465 nm, further preferably 430 nm to 455 nm and particularly preferably 435 nm to 450 nm, and such wavelength band can preferably be used where the amount of fluorescence from the target sample is derived from 7-amino-4-methyl-coumarin or a fluorescent compound similar to 7-amino-4-methyl-coumarin, which is contained in the sample.

It is preferable that the fluorescence detection part in the fluorescence measurement device according to the present invention further include an interference filter. Although irradiation with excitation light in the fluorescence measurement method according to the present invention is not performed toward the upper portion, it is impossible to completely eliminate the effect of overlapping of the half-value width of the excitation light which the excitation light source has due to, e.g., internal reflection and scattering, and thus, it is preferable to provide a configuration in which fluorescence is guided to a light-receiving element using an interference filter that cuts the excitation light off and transmits a particular wavelength band corresponding to fluorescence, and for example, where a target fluorescent sample is 7-amino-4-methyl-coumarin or a fluorescent compound similar to 7-amino-4-methyl-coumarin, the particular wavelength band for the interference filter is preferably 430 nm to 455 nm, more preferably 432 nm to 452 nm and further preferably 435 nm to 450 nm.

For the fluorescence detection part in the fluorescence measurement device according to the present invention, one including a display means for quantifying and displaying an intensity of detected fluorescence and a computer for data processing is preferable, and for such quantification and display means and the computer for data processing, marketed products can be used. For the display means, one capable of transmitting data relating to measurement to a higher-order system linked thereto as necessary, performing data analysis and data processing according to the respective purposes, and providing display in a desired display format in terms of items to be displayed, according to a preset reference or an instruction from an input device, is preferable.

Example of the target liquid sample can include extracted liquid, ground liquid and scattering suspension of a solid sample such as a cell, a tissue or an organ in addition to liquid samples such as gingival effusion, saliva, blood, urine, sweat and tear, and around 10 μL is enough for an amount of a target liquid sample necessary in the fluorescence measurement method according to the present invention, and thus, with only an amount of sample at a tapered tip portion of the microtube, the amount of fluorescence from the target sample can be measured. For example, where the activity of a particular enzyme in the target sample is measured, a fluorescently-labeled substrate obtained by labeling a substrate for such particular enzyme by a fluorescent substance is added to the target liquid sample, and the amount of fluorescence from the target liquid sample is measured as an amount of fluorescence from the fluorescent substance liberated as a result of action of the particular enzyme, and more specifically, the amount of fluorescence from the target liquid sample can be measured by charging a sample obtained from a subject into the microtube together with a fluorescently-labeled substrate for an enzyme expected to be included in the sample.

Examples of the enzyme can include trypsin, chymotrypsin, elastase, subtilisin, collagenase, gingipain, dentilisin, neutrophil elastase, thrombin, glucosidase and acid glucosidase. Also, examples of the fluorescently-labeled substrate can include iBoc-Gly-Gly-Arg-MCA (isobutyloxycarbonyl-glycyl-glycyl-L-arginine-7-amino-4-methylcoumarinamide) on which gingipain or trypsin acts, and various types of peptidyl Lys(Ac)-MCA obtained by binding acetylated lysine and 7-amino-4-methyl-coumarin to a carboxy terminal of oligopeptide such as SEQ ID NO: 1 Ac-Lys-Gly-Leu-Gly-Lys(Ac)-MCA, Ac-Leu-Gly-Lys(Ac)-MCA and Boc-Gly-Lys(Ac)-MCA having a histone H4-derived sequence on which histone deacetylase (HDAC) acts, SEQ ID NO: 2 Ac-Ser-Arg-His-Lys-Lys(Ac)-MCA having a p53-derived sequence, and SEQ ID NO: 3 Ac-Met-Pro-Ser-Asp-Lys(Ac)-MCA having a tubulin-derived sequence, and can also include peptides having an amino-acid sequence similar to the above obtained by binding of a fluorescent compound similar to 7-amino-4-methyl-coumarin.

Figure 2:
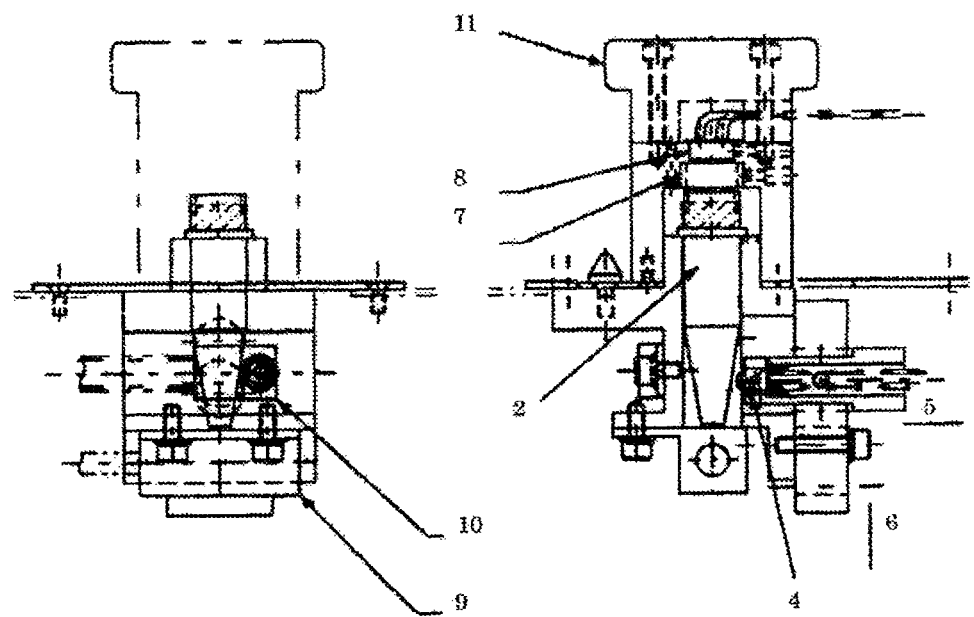
FIG. 2 is a diagram illustrating details of a main part of the fluorescence measurement device according to the present invention.

The fluorescence measurement method and the fluorescence measurement device according to the present invention will specifically be described below with reference to the drawings; however, the present invention is not limited to the embodiment described in these drawings. FIG. 1 illustrates a basic configuration of the fluorescence measurement device according to the present invention, and FIG. 2 illustrates details of a main part of the fluorescence measurement device according to the present invention.

An uncapped microtube 2 charged with a target liquid sample is inserted into a container support part 3 provided inside a measurement box 1, the container support part 3 vertically supporting the microtube 2. An LED 4 that irradiates the microtube 2 laterally in a horizontal direction with excitation light having a particular peak wavelength is attached as an excitation light source, and excitation light having a particular peak wavelength of 365 nm irradiates the target liquid sample inside the microtube. Adjustment for an optimum irradiation light source level is made by a current control part 21 and vertical/horizontal position control parts 5 and 6. The excitation light is distributed to the entire region of the target liquid inside the tube using the sidewall surface as an excitation light waveguide and using the microtube side wall as a waveguide, and the target liquid sample is excited by light leaking from the sidewall surface. Fluorescence generated as a result of the excitation is detected by a light-receiving element 8 at an upper portion of the light-blocking box through a predetermined interference filter 7 (for a center wavelength of 442 nm±10 nm), and input to a signal amplifier 22 (current–voltage conversion amplification+signal amplification: detection range scale adjustment) arranged in a control part inside a control box 20, and the signal is subjected to main control part (PIC+ADC) processing as well as dynamic range adjustment, and the results are informed by a LCD display 23 in terms of predetermined display contents (initial value, final value, time course, state display and temperature display). Where data processing is further necessary, the signal is transmitted from a main control part 24 to a host system 27.

Temperature control for the target liquid sample is performed by a temperature control heater PTC (positive temperature control) 9 provided inside the measurement box in views of fast response and safeness, and temperature control enabling comparison between a feedback signal from a feedback temperature sensor 10 that senses an ambient temperature of a target liquid sample set in the vicinity of the sensor and a program content designed in advance and an output of an instruction to heat an area in the periphery of the target liquid sample as necessary is performed by temperature control parts 25 and 26.

Furthermore, in order to transversely irradiate with excitation light the microtube sidewall, adjustment is performed to optimize vertical and horizontal positions of the LED by the vertical/horizontal position control parts 5 and 6 so that the excitation light can irradiate a substantial surface of the microtube target sample amount, enabling minimization of a background fluorescence level inherent to microtubes.

FIG. 2 illustrates that the main part includes the microtube 2 charged with a target liquid sample, the excitation light source LED 4, the detected light-receiving element 8, the light-receiving interference filter 7, the feedback temperature sensor 10, the temperature control heater PTC 9 and a measurement box upper operation cap 11 and is installed in an intermediate part of the present measurement device.

The container support part 3 disposed inside the measurement box can vertically support the microtube 2, and for example, can vertically support a microtube having any of various types of volumes, 0.2 mL, 1.5 mL and 2.0 mL, particularly a widely-used 1.5 mL microtube.

For a light source for excitation light, a top lens-equipped bombshell-like LED with a peak of 365 nm±10 nm, which is NSHU590B manufactured by Nichia Corporation, is used.

A further specific description of the present invention will be provided by the following examples; however, the present invention is not limited by the examples.

EXAMPLE 1

(Optimization of Position of Excitation Light Source Part)

In the present invention, an amount of fluorescence from a target sample is derived from the Beer's law for an amount of monochromatic light absorbed by a sample, and is expressed by $$F=\phi P(1-10\exp(-abc))$$

if $-abc<0.01$ $$F=2.303\phi Pabc$$

wherein F is a fluorescence intensity,
$\phi$ is a quantum yield
b is an optical path length and
c is a concentration.

Based on the above, optimum component specifications were figured out.

Figure 3:
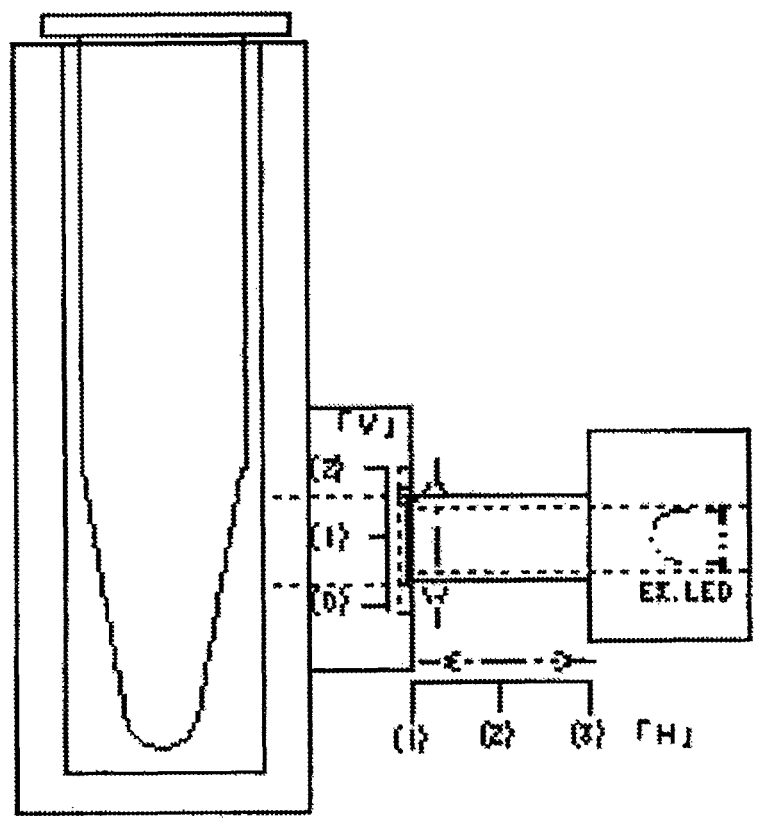
FIG. 3 is a diagram illustrating an arrangement of an excitation light source unit in the fluorescence measurement device according to the present invention.

For the position of the excitation light source part, an examination was conducted for each of cases where a light source is disposed vertically (at V-0, V-1 and V-2) and horizontally (at H(1), (2) and (3)) as illustrated in FIG. 3.

Figure 4:
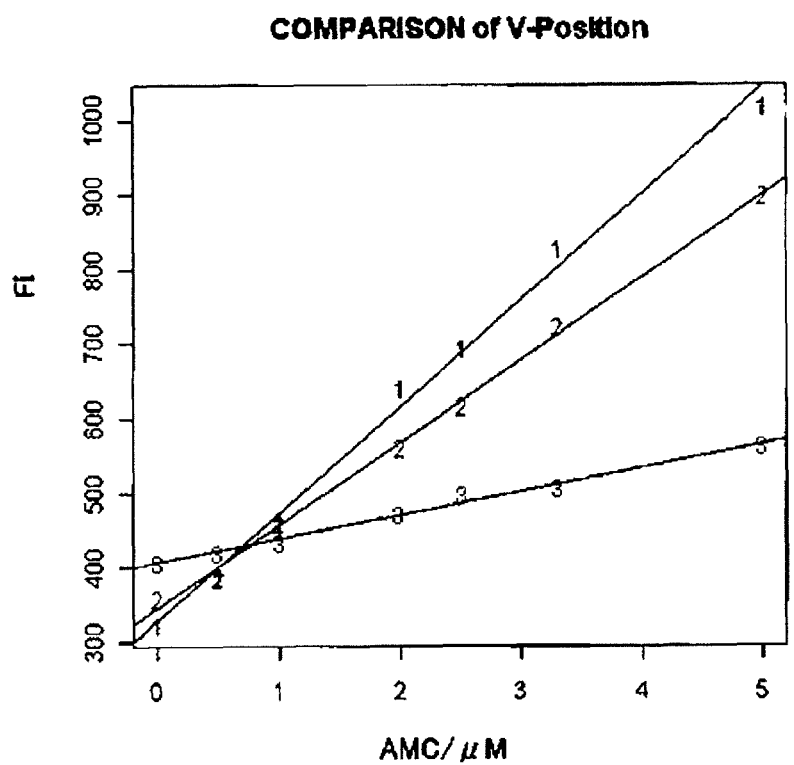
FIG. 4 is a diagram indicating calibration curves obtained by plotting fluorescence intensities (FI) relative to respective AMC standard solutions in each of various arrangements (in a vertical direction) of the excitation light source unit.

For examination for the vertical positions, the light source is fixed horizontally (at H(3)), and FIG. 4 indicates calibration curves with FI intensities plotted relative to 0 to 5 μM AMC standard solutions for the respective V positions: V-0, V-1 and V-2. In the Figure,

1 indicates measurement values at position V-(0);
2 indicates measurement values at position V-(1); and
3 indicates measurement values at position V-(2).

Calibration curve 1 for V-(0), which is a liquid plane, has a largest inclination, which indicates that calibration curve 1 is a calibration curve most suitable for AMC standard solution.

Figure 5:
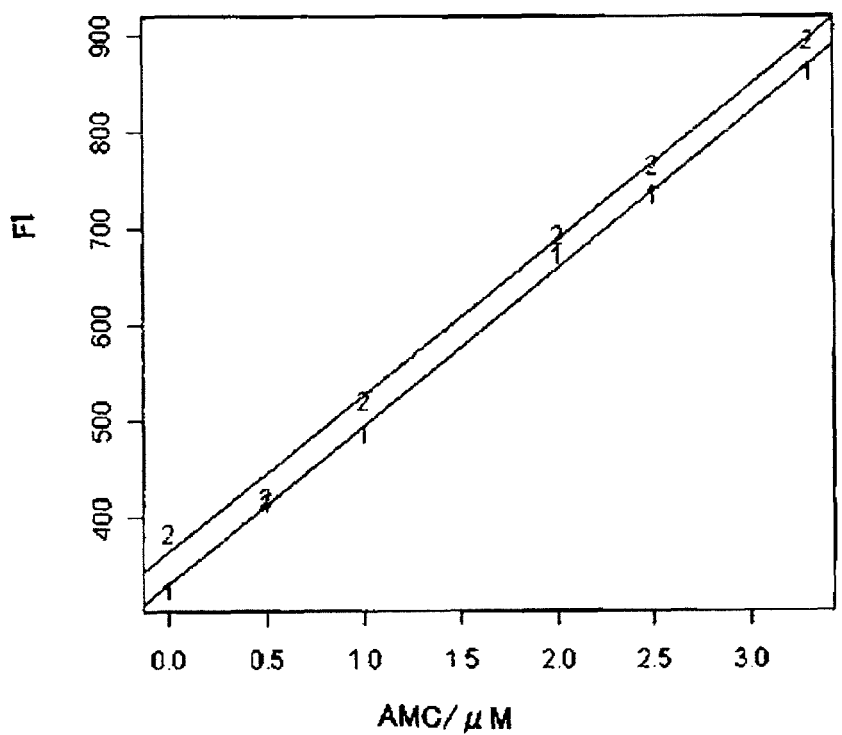
FIG. 5 is a diagram indicating calibration curves obtained by plotting FI intensities relative to respective AMC standard solutions in each of various arrangements (in a horizontal direction) of the excitation light source unit.

Next, horizontal adjustment can be considered as mainly affecting the dynamic range in connection with irradiation energy and irradiation directional characteristic. In FIG. 5, 1 indicates measurement values at position H-(3) and 2 indicates measurement values at position H-(2) (with the vertical position fixed at V-(0)). Measurement values at the position H-(1) are omitted.

EXAMPLE 2

(Fluorescence Intensity vs Product Concentration)

Figure 6:
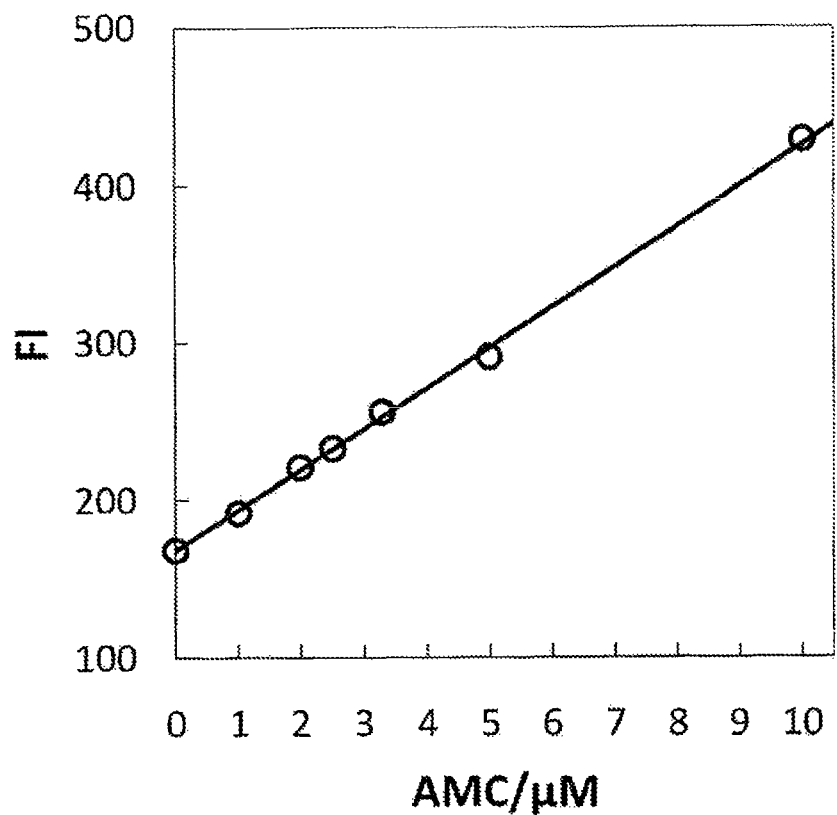
FIG. 6 is a diagram indicating results of fluorescence intensity measurements made in a set condition in which using the fluorescence measurement device according to the present invention, an AMC standard solution was irradiated with light having a peak in a range of 365 nm±10 nm and light of 442 nm was received.

AMC was dissolved in a 0.1 M HEPES buffer with a pH of 7.2 to prepare 1 to 10 μM solutions, and 100 μL of each of the solutions is charged in a microtube (A-1500, manufactured by K.K. Assist, with a volume of 1.5 mL, a length of 450 mm, a length below a threaded cap stopper of 350 mm, a tapering position of 20 mm from the bottom, an outer diameter of 10 mm, an inner diameter of 8 mm and a sidewall thickness of 1 mm), and using the fluorescence measurement device according to the present invention illustrated in FIG. 1, the fluorescence intensity was measured with a set condition to irradiate with light having a peak of 365 nm±10 nm and to receive light of 442 nm. FIG. 6 indicates the results. A substantially linear relationship was indicated between the fluorescence intensity and the AMC concentration. The results indicate that the present invention enables sensing fluorescence from AMC with a high sensitivity to measure the AMC concentration.

EXAMPLE 3

(Fluorescence Intensity vs Trypsin Concentration)

Figure 7:
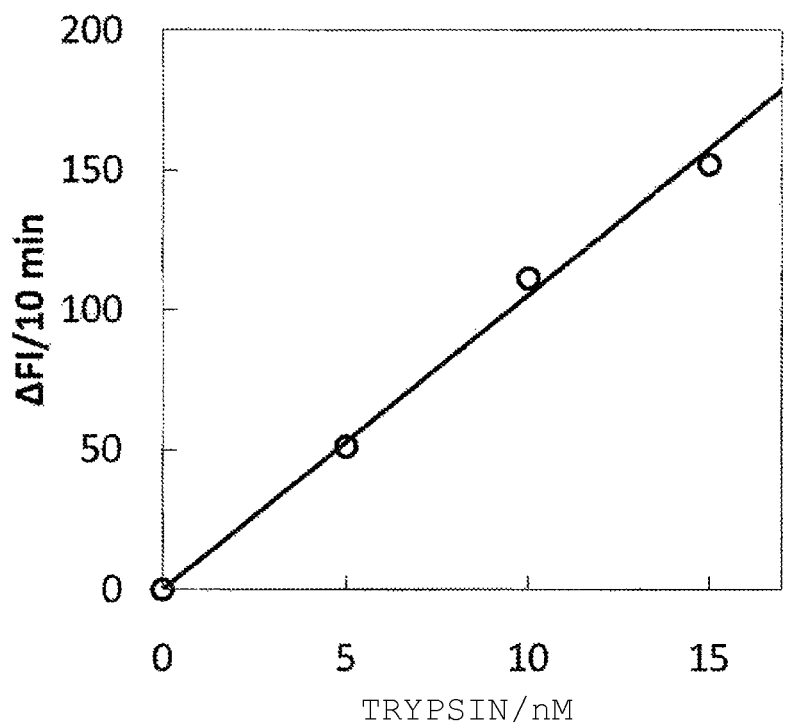
FIG. 7 is a diagram indicating results of fluorescence intensity measurements made in a set condition in which using the fluorescence measurement device according to the present invention, trypsin was made to act on a substrate solution which was then irradiated with light having a peak in a range of 365 nm±10 nm and light of 442 nm was received.

$^i$Boc-Gly-Gly-Arg-MCA was dissolved in a 0.1 M HEPES buffer with a pH of 7.2 and 100 μL of the resulting solution was charged into a microtube (A-1500), and 5 μL of a trypsin solution with an adjusted concentration was added and then fluorescence intensity measurement was conducted for ten minutes to obtain differences in fluorescence intensity ΔFI for the ten minutes. FIG. 7 indicates the results. Where the ΔFI-trypsin concentration relationship was plotted, a linear correlation was obtained. From the results, it was confirmed that according to the present invention, a rate for trypsin to cut AMC out using $^i$Boc-Gly-Gly-Arg-MCA as a substrate can be measured from a rise in AMC concentration.

EXAMPLE 4

(Fluorescence Intensity vs Periodontal Pocket Depth)

Figure 8:
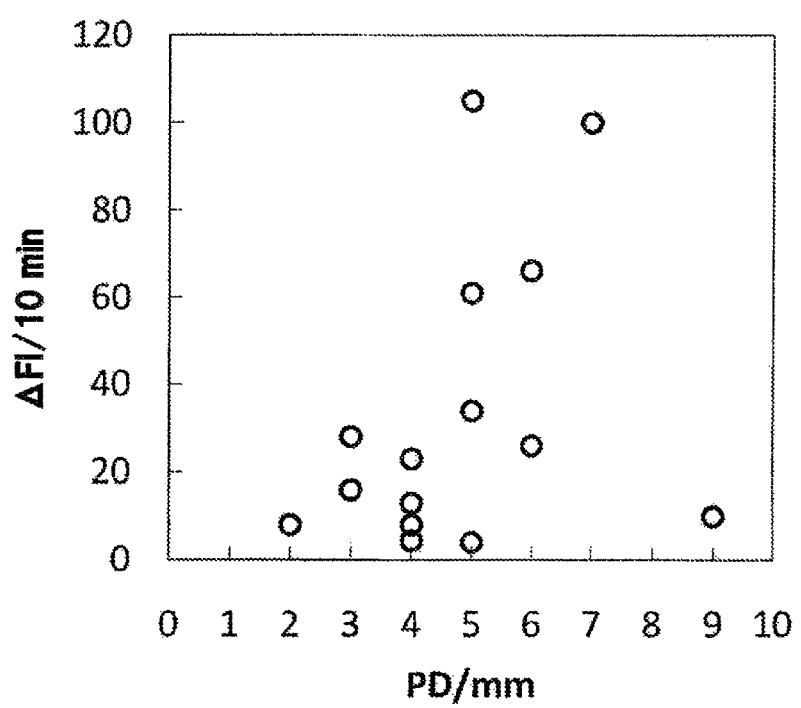
FIG. 8 is a diagram indicating results of fluorescence intensity measurements made in a set condition in which using the fluorescence measurement device according to the present invention, a gingival effusion from a patient with a periodontal disease was made to act on a substrate solution which was then irradiated with light having a peak in a range of 365 nm±10 nm and light of 442 nm was received.

$^i$Boc-Gly-Gly-Arg-MCA was dissolved in a 0.1 M HEPES buffer with a pH of 7.2 and 100 μL of the resulting solution was charged into a microtube (A-1500), 0.1 μL of gingival effusion of a patient with a periodontal disease was obtained via a paper point and this was used as a sample and added into the $^i$Boc-Gly-Gly-Arg-MCA solution inside the microtube. Fluorescence intensity measurement was conducted for ten minutes, and differences in fluorescence intensity ΔFI for the ten minutes were plotted relative to periodontal pockets (pocket depth: PD) measured by a dentist. FIG. 8 indicates the results. From the results, it was confirmed that an enzyme activity of the enzyme Arg-gingipain produced by *P. gingivalis*, which is a periodontal disease-causing bacterium, Arg-gingipain having an ability of cutting AMC out, in gingival effusion is measured to determine whether or not the periodontal disease is in an active phase, which is effective for formulating a therapeutic strategy.

EXPLANATION OF LETTERS OR NUMERALS

1 measurement box
2 microtube
3 container support part
4 LED
5 vertical position control part
6 horizontal position control part
7 interference filter
8 light-receiving element
9 temperature control heater PTC
10 temperature sensor
11 measurement box upper operation cap
20 control box
21 current control part
22 signal amplifier
23 LCD display
24 main control part
25 temperature control part (1)
26 temperature control part (2)
27 host system

The invention claimed is:

1. A fluorescence measurement method comprising loading a microtube charged with a target liquid sample into a light-blocking measurement box, irradiating the microtube that is uncapped laterally in a horizontal direction with excitation light having a particular peak wavelength, and measuring an amount of fluorescence from the target liquid sample excited by light distributed to an entire region of the target liquid inside the tube using a sidewall surface of the microtube as an excitation light waveguide and light leaking from the sidewall surface by a fluorescence detection part for a particular wavelength range provided at an upper portion of the measurement box and above the loaded microtube.

2. The fluorescence measurement method according to claim 1, wherein an ambient temperature of the target liquid sample is controlled.

3. The fluorescence measurement method according to claim 1, wherein excitation light having a wavelength band of 355 nm to 375 nm is used for irradiation.

4. The fluorescence measurement method according to claim 1, wherein an LED is used as a light source for the excitation light.

5. The fluorescence measurement method according to claim 1, wherein the microtube is a plastic microtube that does not block the excitation light.

6. The fluorescence measurement method according to claim 1, wherein the amount of fluorescence from the target sample is an amount of fluorescence having a wavelength band of 430 nm to 455 nm.

7. The fluorescence measurement method according to claim 1, wherein the amount of fluorescence from the target sample is derived from 7-amino-4-methyl-coumarin or a fluorescent compound similar to 7-amino-4-methyl-coumarin contained in the sample.

8. A fluorescence measurement device comprising:
- a light-blocking measurement box to which a microtube is loaded;
- a container support part disposed inside the measurement box, the container support part vertically supporting the microtube;
- an excitation light source part disposed inside the measurement box, the excitation light source part including a light source that horizontally irradiates with excitation light a sidewall surface of the loaded microtube; and
- a fluorescence detection part provided at an upper portion of the measurement box and above the loaded microtube, the fluorescence detection part measuring an amount of fluorescence in a particular wavelength range from a target sample.

9. The fluorescence measurement device according to claim 8, wherein the container support part includes a temperature control means capable of adjusting a temperature of the liquid sample inside the microtube.

10. The fluorescence measurement device according to claim 8, wherein the excitation light source part includes an LED light source.

11. The fluorescence measurement device according to claim 8,
wherein the excitation light source part includes a light source position control means for horizontally or vertically adjusting a position to be irradiated with excitation light.

12. The fluorescence measurement device according to claim 8,
wherein the fluorescence detection part includes an interference filter.

13. The fluorescence measurement device according to claim 8,
wherein the fluorescence detection part includes a display means for quantifying and displaying an intensity of detected fluorescence.

14. The fluorescence measurement device according to claim 8,
wherein the fluorescence detection part includes a computer for data processing.

15. A periodontal disease diagnostic device comprising the fluorescence measurement device according to claim 8.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: acetylated Lysine
<222> LOCATION: (1)..(1)
<220> FEATURE:
<221> NAME/KEY: acetylated Lysine
<222> LOCATION: (5)..(5)
<220> FEATURE:
<221> NAME/KEY: 7-amino-4-methylcoumarinamide
<222> LOCATION: (6)..(6)

<400> SEQUENCE: 1

Xaa Gly Leu Gly Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: acetylated Serine
<222> LOCATION: (1)..(1)
<220> FEATURE:
<221> NAME/KEY: acetylated Lysine
<222> LOCATION: (5)..(5)
<220> FEATURE:
<221> NAME/KEY: 7-amino-4-methylcoumarinamide
<222> LOCATION: (6)..(6)

<400> SEQUENCE: 2

Xaa Arg His Lys Xaa Xaa
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: acetylated Methionine
<222> LOCATION: (1)..(1)
<220> FEATURE:
<221> NAME/KEY: acetylated Lysine
<222> LOCATION: (5)..(5)
<220> FEATURE:
<221> NAME/KEY: 7-amino-4-methylcoumarinamide
<222> LOCATION: (6)..(6)

<400> SEQUENCE: 3

Xaa Pro Ser Asp Xaa Xaa
1               5
```